(12) United States Patent
Strobel

(10) Patent No.: US 6,650,724 B2
(45) Date of Patent: Nov. 18, 2003

(54) COMBINED 3D ANGIO-VOLUME RECONSTRUCTION METHOD

(75) Inventor: Norbrrt Strobel, Baiersdorf (DE)

(73) Assignee: Siemens Aktiengesellschaft, Münich (DE)

( * ) Notice: Subject to any disclaimer, the term of this patent is extended or adjusted under 35 U.S.C. 154(b) by 0 days.

(21) Appl. No.: 10/144,289

(22) Filed: May 13, 2002

(65) Prior Publication Data

US 2002/0191735 A1 Dec. 19, 2002

(30) Foreign Application Priority Data

May 11, 2001 (DE) .......................................... 101 22 875

(51) Int. Cl.$^7$ ............................................... G01N 23/00
(52) U.S. Cl. ........................................... 378/4; 378/901
(58) Field of Search ............................ 378/4, 901, 15, 378/17, 98.11, 98.12, 62, 8; 382/128, 130, 132, 134

(56) References Cited

U.S. PATENT DOCUMENTS 5,671,265 A * 9/1997 Andress .................... 378/98.11
5,764,719 A    6/1998 Noettling .................... 378/4
6,219,441 B1 * 4/2001 Hu ........................... 382/131
6,385,285 B1 * 5/2002 Vaillant et al. ............. 378/62
6,501,848 B1 * 12/2002 Carroll et al. .............. 382/128

OTHER PUBLICATIONS

"3D Dental Imaging by Spiral cT," Vannier et al, Proc. SPIE, vol. 2434 (1995), pp. 346–360.

"Reduction of CT Artifacts Caused by Metallic Implants," Kalender et al, Radiology, vol. 164, No. 2 (1987), pp. 576–577.

\* cited by examiner

Primary Examiner—David V. Bruce
Assistant Examiner—Iraki Kiknadze
(74) Attorney, Agent, or Firm—Schiff Hardin & Waite

(57) ABSTRACT

In a 3D angio-volume reconstruction method for a three-dimensional subject based on 2D projection exposures, shadowing artifacts are avoided by producing a 3D angio-volume dataset based on 2D mask images and a 3D angio-volume dataset based on 2D fill images, and a vessel tree is isolated in the fill volume dataset by a segmentation and is added to the mask image volume dataset after scaling.

4 Claims, 1 Drawing Sheet

COMBINED 3D ANGIO-VOLUME RECONSTRUCTION METHOD

BACKGROUND OF THE INVENTION

1. Field of the Invention

The present invention is directed to a 3D angio-volume reconstruction method for a three-dimensional subject based on 2D projection exposures.

2. Description of the Prior Art

Shadow artifacts that are equivalent to metal artifacts occur in native 3D angio-volume reconstruction (volume reconstruction based on 2D projection exposures that are acquired with a C-arm apparatus after the injection of the contrast agent). Problems associated therewith are a very low signal-to-noise ratio in the shadow region, a greatly increased relationship of stray radiation to primary radiation, and beam hardening artifacts. These effects lead to dark locations in the image between the vessels filled with contrast agent and lead to stripes that extend over the entire reconstructed region. In particular, the image clarity in the immediate environment of the vessels filled with contrast agent is greatly reduced.

Metal artifacts have long been a problem in conventional CT methods; there are various known correction approaches for these artifacts. These correction methods have in common the fact that metal is viewed as an opaque object due to the finite detector dynamics. Accordingly, the attenuation values measured in the metal shadows are completely ignored and considered unusable. The "hole" projections that thus arise must, however, then be supplemented in order to obtain a complete dataset for the back-projection. The most widespread algorithm from 2D-CT (MAR algorithm) bridges the missing one-dimensional projection data by means of a linear function. Such a procedure, however, is far too complicated in an angio-volume reconstruction, the individual projections of which are acquired with a DSA apparatus (digital subtraction angiography), because of the 2D character of the projection images.

SUMMARY OF THE INVENTION

An object of the present invention is to provide a volume reconstruction method wherein shadow artifacts can be eliminated in a simple way.

This object is inventively achieved by producing a 3D angio-volume dataset $V_1$ based on 2D mask images, and a 3D angio-volume dataset $V_2$ based on 2D fill images, and the vessel tree is isolated in the fill volume dataset $V_2$ by means of a segmentation and is added to the mask image volume dataset $V_1$ after scaling.

According to the inventive method, thus, both mask images, i.e. projection exposures without contrast image, as well as fill images, i.e. projection exposures with contrast agent, are generated in a standard DSA exposure sequence. Due to the absence of contrast agent in the vessels when the mask images are obtained, shadowings do not occur in the volume dataset $V_1$ based on mask images. As a result of superimposition of the segmented vessel tree from the fill volume dataset $V_2$, thus, a complete 3D angio-volume dataset can be produced without any shadowing artifacts whatsoever. A particular advantage of the inventive reconstruction method is that the combination of the 3D datasets can ensue by simple addition. A registration step is not needed for this purpose since both $V_1$ as well as $V_2$ are reconstructed with reference to the same coordinate system. An extremely simple method thus is achieved from presenting low-contrast or medium-contrast subjects artifact-free together with high-contrast vessel trees.

Segmenting of the vessel tree can ensue directly from the fill volume dataset $V_2$, for example by simple thresholding, i.e. setting of thresholds, or by means of region growing, i.e. combining neighboring and/or related voxels (volume elements), with the result being subsequently refined by morphological operations. It has proven especially expedient, however, in a further embodiment of the invention to produce the segmenting of the vessel tree from the difference volume dataset $V=V_2-V_1$.

DESCRIPTION OF THE PREFERRED EMBODIMENTS

Figure 1:
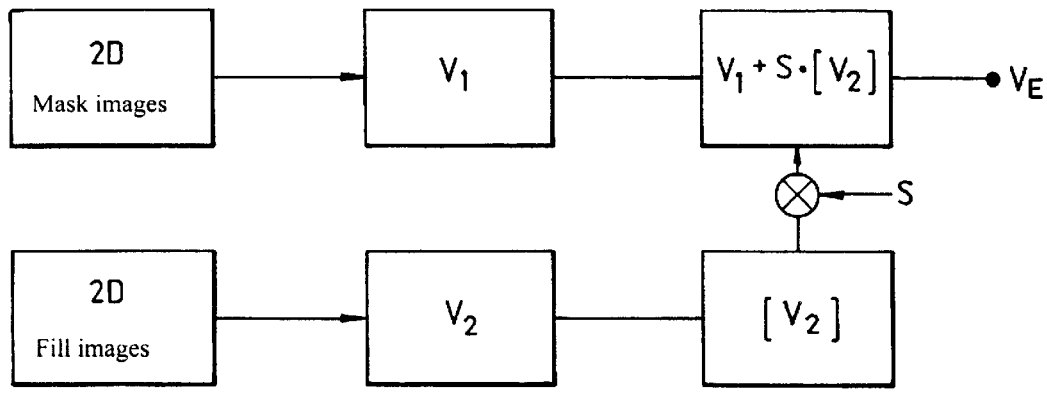
FIG. 1 is a block diagram showing the basic steps for acquiring an artifact-free presentation of a three-dimensional subject with high-contrast vessel trees in accordance with a first embodiment of the invention.

FIG. 1 shows how the volume datasets $V_1$ and $V_2$ are generated from the 2D mask images and the 2D fill images. The vessel tree $[V_2]$ is segmented from the volume dataset $V_2$ by means of a known segmentation method and, following scaling, is superimposed by addition with the mask image volume dataset $V_1$ in order to obtain the ultimate volume dataset $V_E$.

Figure 2:
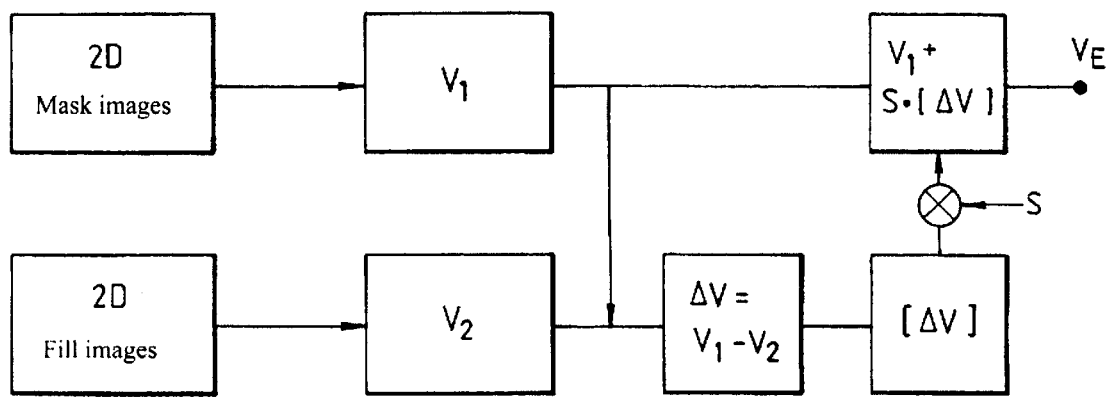
FIG. 2 is a block diagram showing the basic steps for acquiring an artifact-free presentation of a three-dimensional subject with high-contrast vessel trees in accordance with a second embodiment of the invention.

In the reconstruction method according to FIG. 2, the mask image volume dataset $V_1$ is initially subtracted from the fill volume dataset $V_2$ after the production of the volume datasets $V_1$ and $V_2$, and the vessel tree filled with contrast agent is segmented from the resulting difference volume $\Delta V$. This can be achieved significantly more cleanly and with higher contrast than when the fill volume dataset $V_2$ is directly extracted. The segmented difference volume $[\Delta V]$ is in turn scaled and added to the mask image volume dataset $V_1$. The ultimate volume dataset $V_E$ is finally obtained.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for 3D angio-volume reconstruction of a three-dimensional subject based on 2D projection exposures, comprising the steps of:

obtaining a plurality of 2D mask images of a three-dimensional subject with no contrast agent in said subject and producing a 3D angio-volume dataset $V_1$ based on said 2D mask images;

obtaining a plurality of 2D fill images of said subject, with contrast agent in said subject, and producing a 3D angio-volume dataset $V_2$ based on said 2D fill images, said dataset $V_2$ containing a vessel tree made visible by said contrast agent; and isolating said vessel tree in said dataset $V_2$ by segmentation, scaling the isolated vessel tree to obtain a scaled isolated vessel tree, and adding said scaled isolated vessel tree to said dataset $V_1$ to produce a 3D angio-volume reconstruction without shadowing artifacts.

2. A method as claimed in claim 1 wherein the step of segmenting said vessel tree comprises forming a difference volume dataset $\Delta V=V_2-V_1$.

3. A method as claimed in claim 1 wherein the step of segmenting said vessel tree comprises subjecting said dataset $V_2$ to a thresholding operation.

4. A method as claimed in claim 1 wherein the step of segmenting said vessel tree comprises growing regions in said dataset $V_2$ to obtaining a resulting dataset, and refining said resulting dataset by at least one morphological operation.

* * * * *